United States Patent [19]
Bechmann

[11] Patent Number: 6,031,463
[45] Date of Patent: Feb. 29, 2000

[54] LOAD SIGNALING DEVICE FOR A PATIENT'S FOOT

[75] Inventor: Peter Bechmann, Oberammergau, Germany

[73] Assignee: SANOSTEP Gesellschaft fur innovative Gesundheitstechnik mbH, Englfing, United Kingdom

[21] Appl. No.: 09/175,196

[22] Filed: Oct. 20, 1998

[30] Foreign Application Priority Data

Oct. 21, 1997 [DE] Germany .................... 297 18 680

[51] Int. Cl.[7] ........................................ G08B 21/00
[52] U.S. Cl. .................. 340/666; 340/272; 340/573; 340/685; 128/779; 128/2 S; 73/862.625; 73/172; 364/556; 36/136
[58] Field of Search ................... 340/666, 272, 340/573, 685; 128/779, 2 S; 364/556; 73/862.625, 172; 36/136

[56] References Cited

U.S. PATENT DOCUMENTS

| | | | |
|---|---|---|---|
| 3,702,999 | 11/1972 | Gradisar | 340/272 |
| 3,791,375 | 2/1974 | Pfeiffer | 128/2 S |
| 3,974,491 | 8/1976 | Sipe | 340/272 |
| 4,745,930 | 5/1988 | Confer | 128/799 |
| 5,253,654 | 10/1993 | Thomas et al. | 128/799 |
| 5,323,650 | 6/1994 | Fullen et al. | 73/172 |
| 5,357,696 | 10/1994 | Gray et al. | 36/136 |
| 5,408,873 | 4/1995 | Schimdt et al. | 73/862.625 |

*Primary Examiner*—Jeffery A. Hofsass
*Assistant Examiner*—Tai T. Nguyen
*Attorney, Agent, or Firm*—Ratner & Prestia

[57] ABSTRACT

A device for providing an acoustic signal to a patient when a predetermined load is placed on the patient's foot comprises a fluid filled control means with a first bladder underlying the patient's foot and a second bladder as interconnected via a flexible tube. The second bladder is adapted to actuate a signaling means comprising a resiliently supported and biased click spring that provides an audible click noise when actuated by the second bladder of the control means at a predetermined pressure of the liquid corresponding to a predetermined load as placed on the patient's foot.

7 Claims, 4 Drawing Sheets

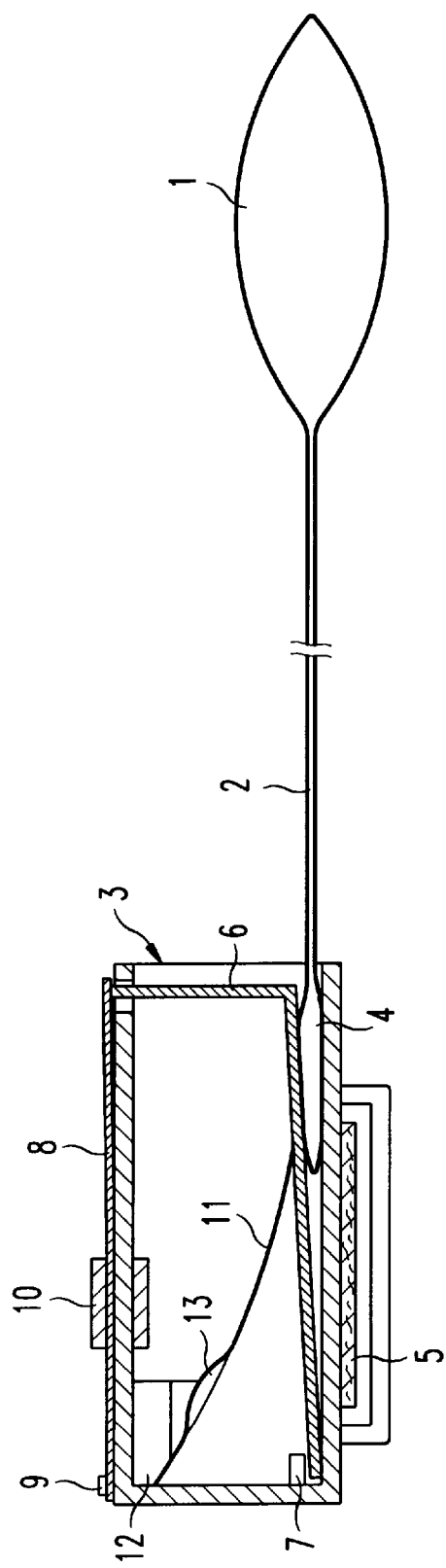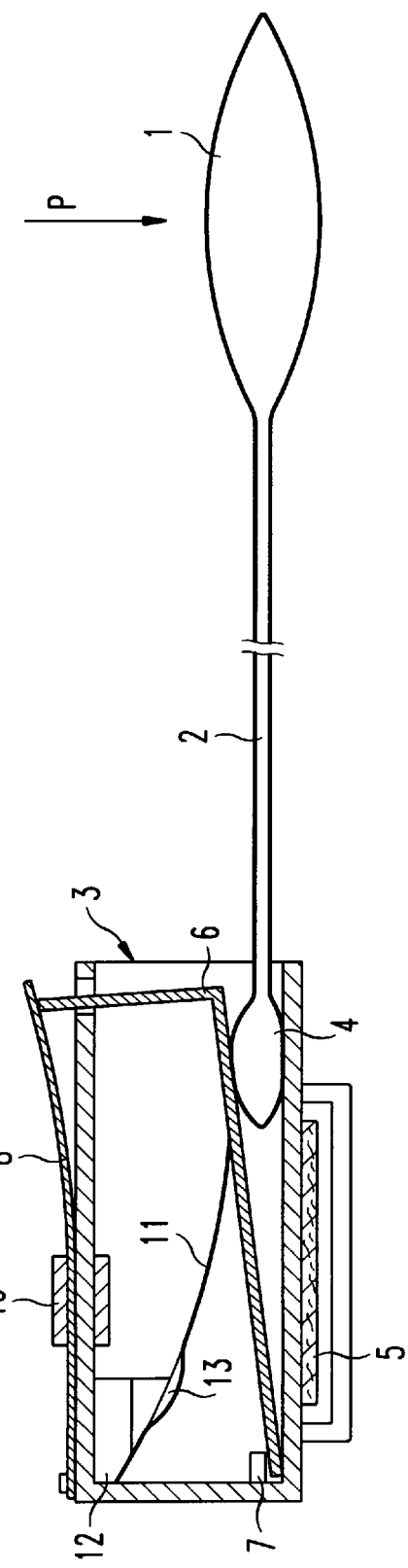

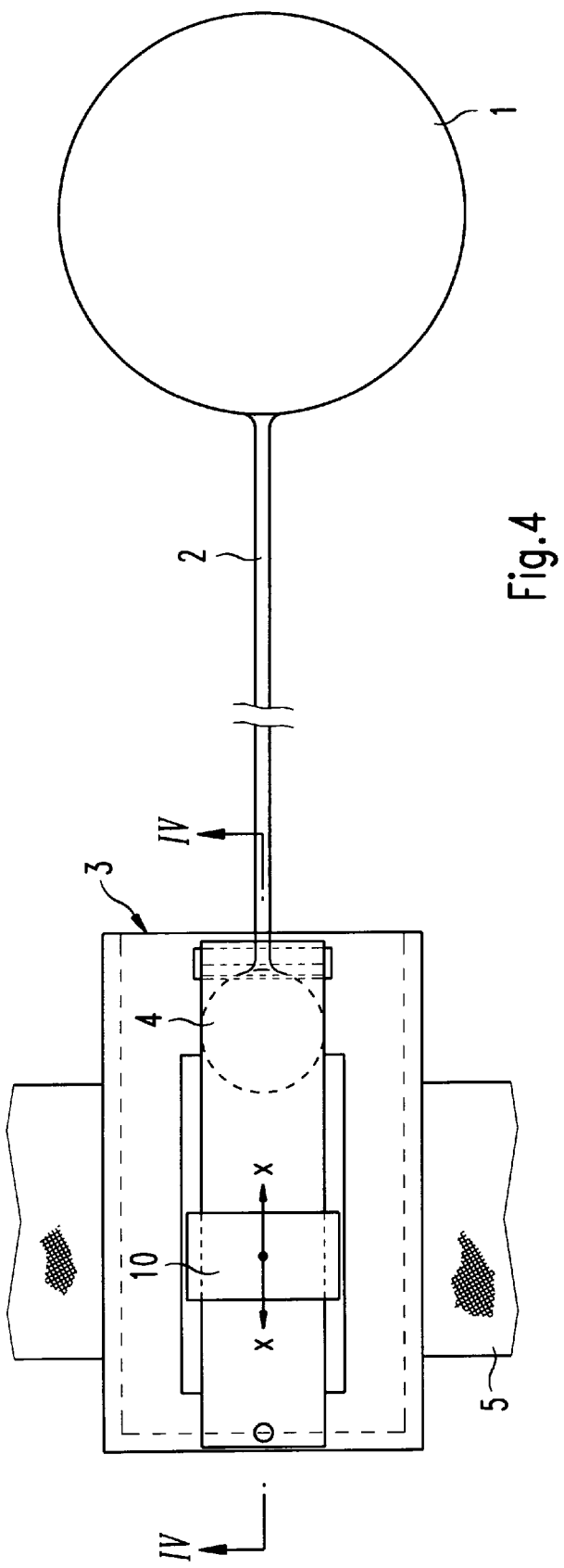
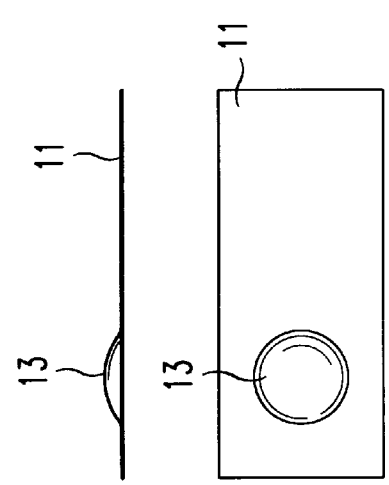

LOAD SIGNALING DEVICE FOR A PATIENT'S FOOT

BACKGROUND OF THE INVENTION

This invention relates to a device for providing an acoustic signal to a patient when a predetermined load is placed on the patient's foot.

Devices of the above kind are used for warning the patient in those cases where due to a fracture of a leg or other orthopedic surgery operations the load on the leg as related to the patient's weight must be limited. With respect to the therapy of less complicated leg fractures an initial load on the patient's foot of only about 20 kg is considered as an allowable limit when the patient will start with his first attempts to walk after an operation of his fractured leg whereby such a lowermost load will then subsequently be increased stepwise to thereby secure a correct healing or recovery of the operated leg.

A prior art device as described in U.S. Pat. No. 3,974,491 comprises a resilient foot pad adapted to overlie the inner sole of a shoe and having a core for example of a foamed plastic which receives a resilient tube being filled with a liquid and extending from adjacent the toe end of the pad to adjacent its heel end with a plurality of loops. The tube of the foot pad is connected via a tube connector to a resilient bladder which serves as a pressure responsive means communicating with the liquid. The bladder is to actuate a signaling means at a predetermined pressure of the liquid via a pivotally mounted bell crank lever that engages a control button of a switch which in turn actuates a battery driven buzzer. All of these means are housed within a box which by means of a loop band having a hook and loop fastener may be mounted on the patient's leg. Whenever a buzzer signal is supplied the patient will thusly be warned on having reached a predetermined load on his foot which by means of a compression coil spring biasing the bell crank lever against the bladder may be adjusted within a predetermined range between a still allowable lowermost load on the patient's foot and increasing higher load values.

Since with such known devices the signaling means comprises electrical means such as a switch and a battery driven buzzer as well as interconnecting wires it is quite apparent that thereby the costs for producing the device and those for maintaining the service of such devices are high whereby also the operation of these devices may as well not be considered as perfectly reliable.

BRIEF SUMMARY OF THE INVENTION

The present invention deals with the object of providing a less expensive and at the same time more reliable load signaling device for a patient's foot of the kind as above referred for warning the patient by an audible signal when a predetermined load placed on his foot has been reached.

A device for providing an acoustic signal to a patient when a predetermined load is placed on the patient's foot comprises according to the present invention a resilient foot pad preferably in the form of a bladder and filled with a fluid serving as a pressure sensor for the patient's weight and sensing the load exerted via the patient's foot to the foot pad. A fluid line connects the resilient foot pad to a pressure responsive means preferably also in the form of a bladder and communicating with the liquid so that thereby an autonomous body filled with the fluid is obtained as a separate exchangeable control means for actuating a signaling means. The signaling means comprises a click spring having a deformable bulge. This spring is resiliently supported preferably within a box which serves as a resonance body in such a manner as to supply an audible click noise when actuated by the pressure responsive means. The click noise is obtained by a transient deformation of the projecting bulge whenever the click spring is leaving its rest position and is subsequently again returning to the same. The signaling means of the device according to the present invention thusly provides a very simple mechanical embodiment which yet is very effective in its warning capabilities.

BRIEF DESCRIPTION OF THE DRAWINGS

FIG. 2 is a vertical section of the box for mounting the click spring and a pressure responsive means of the device taken on the plane indicated by the line IV—IV in FIG. 4 whereby no load is exerted on an interconnected pressure sensor of the device;

FIG. 3 is a vertical section similar to FIG. 2 and showing the device when a load is exerted on the pressure sensor;

FIG. 4 is an elevational view of the device;

FIG. 5 is a side view and a plan view of the click spring; and

DETAILED DESCRIPTION

Figure 1:
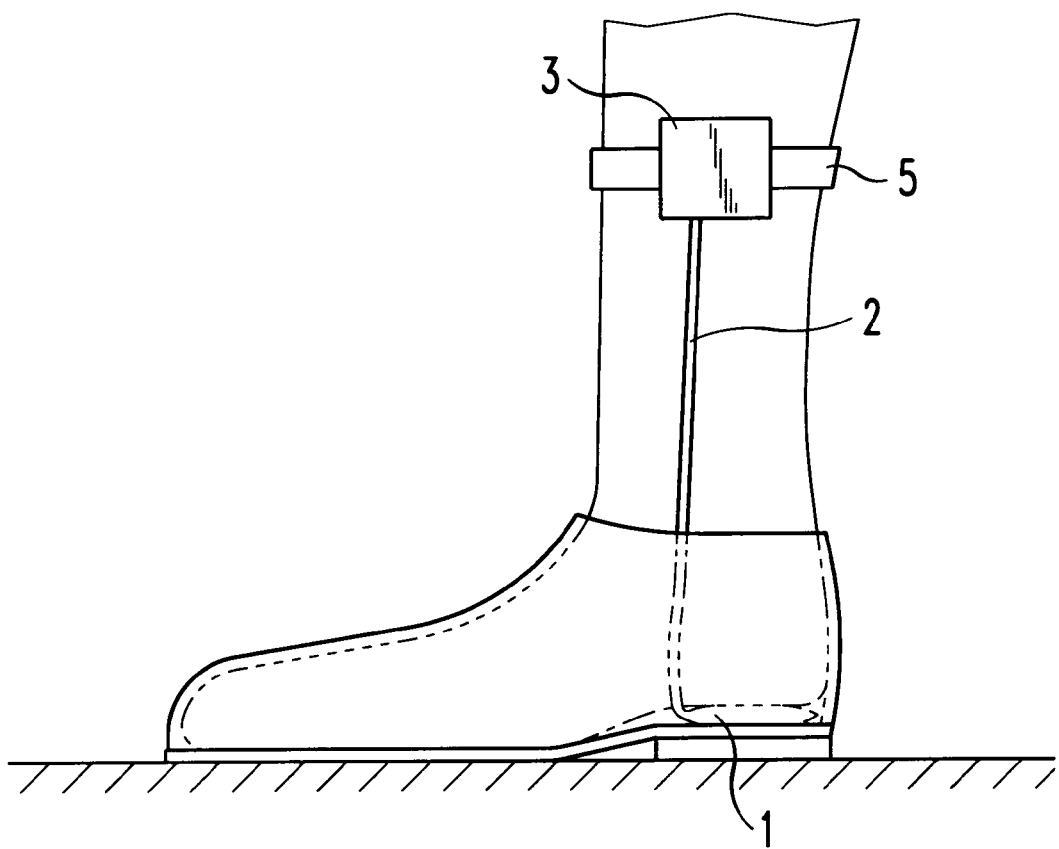
FIG. 1 is a side view of a device in accordance with a first embodiment of the invention.
Figure 6:
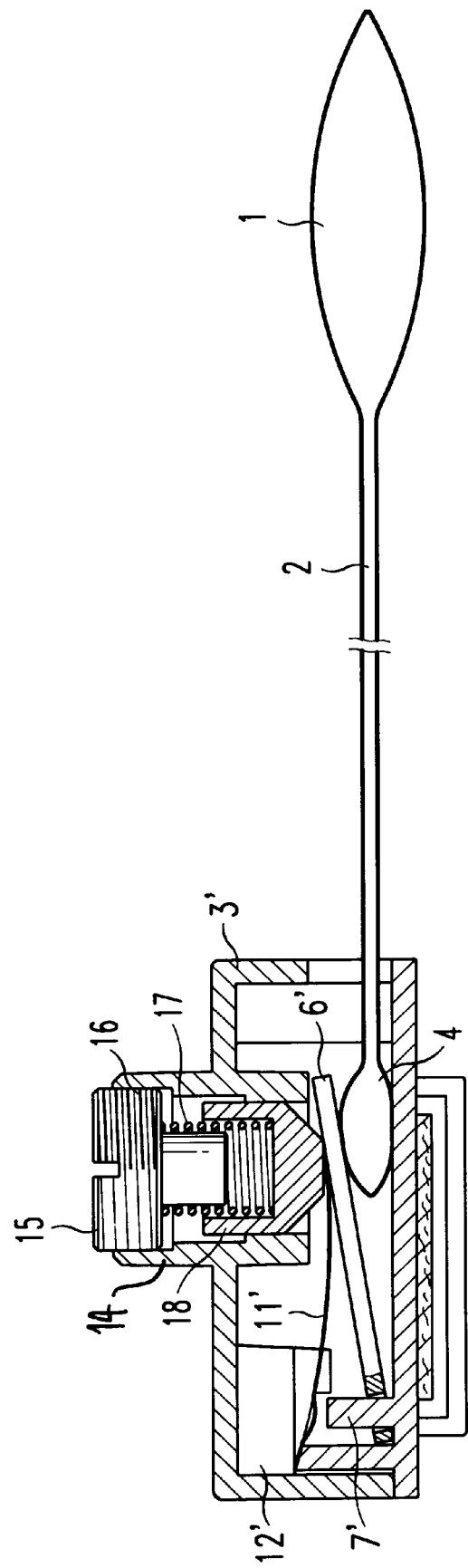
FIG. 6 is a vertical section similar to FIG. 3 of the device according to a second embodiment of the invention.

A device in accordance with the invention is to be mounted on a patient's fractured leg for warning the patient when a predetermined load placed on his foot has been reached. The device comprises a resilient foot pad 1 filled with a fluid such as water which serves as a pressure sensor for the patient's weight for sensing the load exerted via the patient's foot to the foot pad. The resilient foot pad or pressure sensor 1 is formed as a bladder for underlying the patient's foot heel and/or any other sole portion. It is connected via a flexible tube 2 to a pressure responsive means having also the form of a bladder 4 which is arranged within a box 3 that is mounted on the patient's leg by means of a loop band 5. It should be noted here that the two bladders 1 and 4 as well as the interconnecting tube 2 form an autonomous body as a separate exchangeable control means which is filled with water and comprises two plastic foils one above the other which are fixed together for example by means of a continuous weld seam after having been filled with a predetermined amount of water as a pressure medium sensing the patient's weight as placed on the foot of his fractured leg.

The water filled bladder 4 is underlying a L-shaped actuating lever 6 which is arranged inside of the box 3. The one leg of this lever has an abutment as formed by a post 7 and in cooperation with the bottom of the box. The free end of the other leg of the lever 6 passes through an opening in the upper wall of the box 3 and is in contact with the free end of a leaf spring 8 the other end of which has a fixation point 9 on the box for obtaining a biasing force of the leaf spring 8 against the lever 6 and therefore also against the water filled bladder 4 of the autonomous control means. This biasing force of the leaf spring 8 may be adjusted to a predetermined value by means of a slide member 10 whereby with a relative predetermined rest position the biasing force acting via the lever 6 on the bladder 4 is for example adjusted to such a value that at a predetermined load of for example 20 kg as placed on the patient's foot and then transmitted by the fluid of the pressure sensor 1 via the tube 2 to the bladder 4 will then move the lever 6 from its rest position shown in FIG. 2 to an actuated position as shown in FIG. 3. By moving the slide member 10 in the direction of the arrows X—X in FIG. 4 the biasing force of the leaf spring 8 will either be decreased with a motion to the left or will be increased by a motion to the right of this slide member.

The control means formed by the water filled bladders 1, 4 and the interconnecting tube 2 is adapted to actuate a signal means which comprises a simple click spring 11 which is supported by its two ends on a post 12 of the box 3 and on the L-shaped lever 6, respectively. The click spring 11 has a deformable bulge 13 that provides a source for a click noise being supplied whenever the click spring is moved from its rest position shown in FIG. 2 to its signaling position shown in FIG. 3 and vice versa. This click noise is obtained by a transient deformation of the bulge 13 causing a change between its upwardly directed projection in the rest position to a downwardly directed projection in the signaling position. The same click noise is obviously also obtained when the click spring is returned from its signaling position to its rest position as soon as the load placed on the patient's foot is decreased to a value lower than the predetermined load which is initially adjusted by means of the slide member 10. Since the box 3 may be considered as a resonance body such a click noise of the click spring 11 will receive an amplification. The click noises as produced by the click spring 11 and its deformable bulge 13, will thusly be more positively transmitted to the patient as a warning signal for causing him to decrease the load on the foot of his fractured leg.

FIG. 2 shows a second embodiment of the device according to the present invention. The fluid filled bladder 4 is underlying a pressure plate 6' which is pivotally arranged on a post 7' more or less in the same manner as the one leg of the lever 6 of the above described first embodiment of the inventive device. This pressure plate 6' supports one end of a click spring 11' the other end of which is supported on a post 12'. The click spring 11' is biased by a pull-back spring acting in the same manner as the leaf spring 8 and provided in this case by a compression coil spring 17. The compression coil spring 17 acts between a set screw 15 which engages an outwardly projecting sleeve 14 of the box 3' by means of a thread 16 and is supported on a feeler 18 which slidably engages an inner projection of the sleeve 14 and is in contact with the pressure plate 6'. The biasing force of the compression coil spring 17 acting via the feeler 18 against the pressure plate 6' and further against the bladder 4 will therefore be increased by moving the set screw 15 more inwardly whereas it will be decreased when the set screw 15 is moved more outwardly. The set screw 15 therefore acts in the same manner as the slide member 10 in the sense of adjusting the load signaling device to any predetermined warning signal as obtained by the click noise of the click spring whenever a predetermined load is placed on the patient's foot.

What is claimed is:

1. A device for providing an acoustic signal to a patient when a predetermined load is placed on the patient's foot comprising:

a resilient foot pad filled with a fluid and serving as a pressure sensor for the patient's weight for sensing the load exerted via the patient's foot to the foot pad; and a fluid line connecting the resilient foot pad to a pressure responsive means communicating with the liquid and adapted to actuate a signaling means at a predetermined pressure of the liquid corresponding to a predetermined load when placed on the patient's foot;

wherein said signaling means comprises a click spring having a deformable bulge and being resiliently supported such as to supply an audible click noise when actuated by said pressure responsive means whereby the click noise is obtained by a transient deformation of the bulge whenever the click spring is leaving its rest position and is again returning to the same.

2. The device of claim 1 in which the click spring is arranged within a box serving as a resonance body for amplifying its click noise.

3. The device of claim 1 in which the click spring is biased against a lever which is in operational contact with the pressure responsive means and adapted to actuate the click spring for supplying its click noise.

4. The device of claim 1 in which the click spring is biased by a pull-back spring.

5. The device of claim 1 in which the click spring is biased by a leaf spring which is fixed to the box in such a manner that its biasing force acting via a lever against the pressure responsive means may be adjusted by a slide member to thereby adjust the predetermined load at which the click spring will supply its click noise.

6. The device of claim 1 in which the click spring is biased by a compression coil spring acting between a feeler which is in contact with the click spring and an adjustable set screw.

7. The device of claim 1 in which the resilient foot pad and the pressure responsive means are both provided by a bladder of a resilient material and are interconnected by a flexible tube to thereby obtain an autonomous body filled with fluid as a separate exchangeable control means for actuating the click spring.

* * * * *

UNITED STATES PATENT AND TRADE MARK OFFICE
CERTIFICATE OF CORRECTION

PATENT NO. : 6,031,463
DATED : February 29, 2000
INVENTOR(S) : Bechmann

It is certified that error appears in the above-identified patent and that said Letters Patent is hereby corrected as shown below:

ON THE TITLE PAGE:

The Assignee should be correctly listed as:

[73]  Assignee:  SANOSTEP Gesellschaft fur
innovative Gesundheitstechnik mbH.
Englfing, Germany Signed and Sealed this Twenty-fourth Day of April, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,031,463
DATED : February 29, 2000
INVENTOR(S) : Bechmann

It is certified that error appears in the above-identified patent and that said Letters Patent is hereby corrected as shown below:

Title page,
The Assignee should be correctly listed as:
[73] Assignee: SANOSTEP Gesellschaft fur
innovative Gesundheitstechnik mbH.
Eglfing, Germany This Certificate supersedes Certificate of Correction issued April 24, 2001.

Signed and Sealed this

Nineteenth Day of February, 2002

*Attest:*

JAMES E. ROGAN
*Attesting Officer*     *Director of the United States Patent and Trademark Office*